United States Patent [19]

Arai et al.

[11] Patent Number: 5,141,302
[45] Date of Patent: Aug. 25, 1992

[54] INTRAOCULAR LENGTH MEASURING INSTRUMENT

[75] Inventors: Akihiro Arai; Hideki Hatanaka; Akihiko Sekine; Isao Minegishi; Fumio Ohtomo, all of Tokyo, Japan

[73] Assignee: Kabushiki Kaisha Topcon, Tokyo, Japan

[21] Appl. No.: 708,133

[22] Filed: May 30, 1991

[30] Foreign Application Priority Data

May 31, 1990 [JP] Japan .................................. 2-145107

[51] Int. Cl.$^5$ .............................................. A61B 3/10
[52] U.S. Cl. .................................... 351/205; 351/211; 351/221
[58] Field of Search ................ 351/204, 205, 206, 207, 351/208, 211, 221; 128/665, 745

[56] References Cited

U.S. PATENT DOCUMENTS 5,042,938 8/1991 Shimozono .......................... 351/205

Primary Examiner—Rodney B. Bovernick
Attorney, Agent, or Firm—Finnegan, Henderson, Farabow, Garrett & Dunner

[57] ABSTRACT

An intraocular length measuring instrument including a light source having a short coherent length, a beam splitter for forming a measuring optical path across the interior of an eye to be tested and a reference optical path within the instrument, and guiding a beam of light from the light source to both the measuring optical path and the reference optical path, a first light receiving portion for interfering light reflected by an intraocular object to be measured after passing along the measuring optical path with light coming through the reference optical path and receiving a resultant interference light, an intraocular object position measuring portion for finding an optical path difference from an optical path length of the reference optical path and a peak position of a signal coming from the first light receiving portion, a light irradiating optical system for irradiating a light beam to the cornea of the eye to be tested, a light receiving optical system for introducing a reflected light from the cornea to a second light receiving portion, and a corneal position measuring portion for fining a position of the cornea from an output of the second light receiving portion.

4 Claims, 13 Drawing Sheets

INTRAOCULAR LENGTH MEASURING INSTRUMENT

BACKGROUND OF THE INVENTION

1. Field of the Invention

This invention relates to an intraocular length measuring instrument for measuring an intraocular length between an intraocular object to be measured and a corneal vertex by finding a corneal vertex position using an optical system utilizing the principle of geometrical optics and finding a position of an intraocular object to be measured using an interference optical system utilizing the principle of physical optics.

2. Brief Description of the Prior Art

Heretofore, an eye axis length measuring instrument is known, in which a light beam from a laser diode LD is irradiated to an eye to be tested and a plane wave reflected from the eye fundus as an intraocular object to be measured is caused to interfere with a spherical wave reflected from the cornea, and a length (eye axis length), as one kind of intraocular length, between the eye fundus and the cornea is measured using the interference signal.

However, this conventional eye axis length measuring instrument has such shortcoming as that when a plane wave reflected from the eye fundus is caused to interfere with a spherical wave reflected from the cornea, a high accuracy of alignment of the measuring instrument is strictly required with respect to an eye to be tested and this is, in a sense, a vital shortcoming for an instrument which is intended to measure a constantly moving eye ball. If the alignment of the measuring instrument is deviated, even in a slightest amount, with respect to the eye, positions of interference fringes are considerably deviated and the number of interference fringes is suddenly increased at a place from where the eye to be measured has been observed till that time. This makes it difficult to tell whether an interference is taken place between the plane wave and the spherical wave.

SUMMARY OF THE INVENTION

It is therefore a general object of the present invention to provide an intraocular length measuring instrument, in which measurement can be carried out with ease.

A specific object of the present invention is to provide an intraocular length measuring instrument, in which such a high accuracy of alignment as required in a comparable conventional instrument is no more required.

To achieve the above objects, there is essentially provided an intraocular length measuring instrument including a light source having a short coherent length, a beam splitter for forming a measuring optical path via the interior of an eye to be tested and a reference optical path within the instrument, and guiding a beam of light from the light source to both the measuring optical path and the reference optical path, a first light receiving portion for interfering light reflected by an intraocular object to be measured after passing along the measuring optical path with light coming through the reference optical path and receiving a resultant interference light, an intraocular object position measuring portion for finding an optical path difference from an optical path length of the reference optical path and a peak position of a signal coming from the first light receiving portion, a light irradiating optical system for irradiating a light beam to the cornea of the eye to be tested, a light receiving optical system for guiding a reflected light from the cornea to a second light receiving portion, and a corneal position measuring portion for finding a position of the cornea from an output of the second light receiving portion.

According to an intraocular length measuring instrument of the present invention, the position of a corneal vertex is measured using a light irradiating optical system and a light receiving optical system both as a geometrical optics optical system, the position of an intraocular object to be measured is measured using a light source constituting a part of a physical optical system, and this light source utilizes a short coherent length. Accordingly, the positions where interference fringes are taken place can be found with high accuracy.

BRIEF DESCRIPTION OF THE DRAWINGS

The several features and advantages of the present invention will become more apparent to those skilled in the art by reference to the detailed description which follows taken in conjunction with the several figures of the drawing in which:

FIG. 1 is a view showing an optical system of an intraocular length measuring instrument according to the present invention;

FIG. 2 is a view showing a ring image formed on a two-dimensional image sensor shown in FIG. 1;

FIGS. 3 and 4 are explanatory views for schematically explaining the operation of an cornea distance measuring optical system shown in FIG. 1;

FIG. 5 is an explanatory view for explaining detection of a corneal vertex position;

FIG. 6 is an explanatory view of an interference waveform output from a photo sensor shown in FIG. 1;

FIG. 7 is a view showing a full-wave rectification waveform of the interference waveform;

FIG. 8 is a view of a waveform showing a smooth wave of the full-wave rectification waveform;

FIG. 9 is an explanatory view of explaining a processing of the smooth wave;

FIG. 10 is a block diagram of a signal processing circuit;

FIGS. 11 and 12 are explanatory views for finding an eye axis length based on a corneal vertex position and an eye fundus position;

FIG. 13 is an optical diagram showing a cornea distance measuring system thereof;

FIGS. 14 and 15 are views showing an interference optical system thereof;

FIGS. 16 and 17 are schematic optical diagrams showing the operation of the cornea distance measuring system;

FIGS. 18 and 19 are views showing a luminous spot image formed on a two-dimensional image sensor;

FIGS. 20 through 24 are views showing an intraocular length measuring instrument according to a third embodiment of the present invention;

FIG. 20 is an optical diagram showing a cornea distance measuring system thereof;

FIGS. 22 and 23 are explanatory views showing deviation of alignment;

FIG. 24 is an optical diagram showing a modified embodiment of the cornea distance measuring system shown in FIG. 20.

DETAILED DESCRIPTION OF THE EMBODIMENT

First Embodiment

Figure 1:
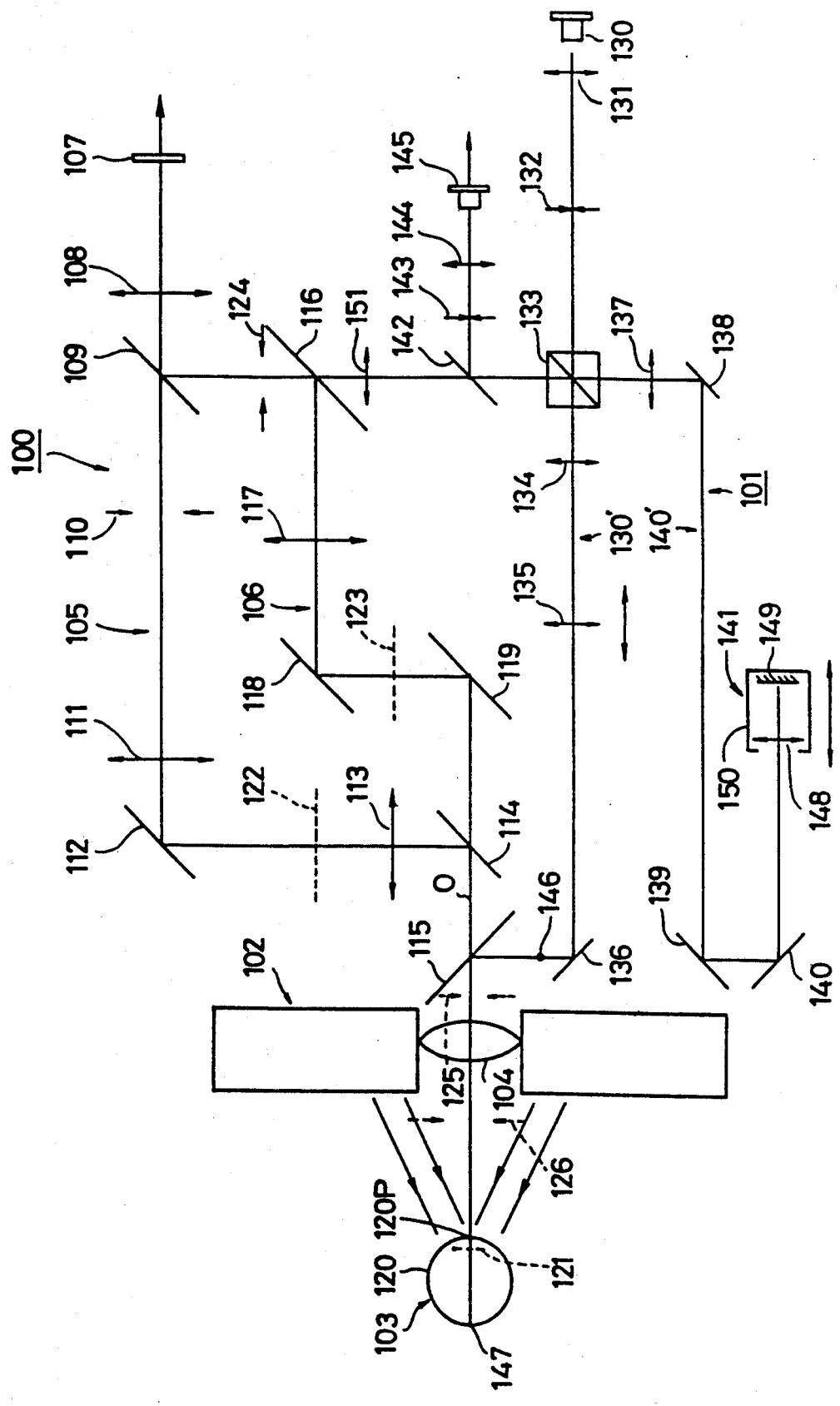
FIGS. 1 through 12 are explanatory views for explaining an intraocular length measuring instrument according to a first embodiment of the present invention.

FIG. 1 shows one embodiment of a cornea distance measuring system in which a corneal vertex position is found by projecting a ring image to the cornea of an eye to be tested.

In FIG. 1, the numeral 100 denotes a cornea distance measuring system, 101 an interference optical system, 102 a ring-shaped light source projecting portion acting as a light irradiating optical system for irradiating a light beam to the cornea of an eye to be tested, 103 the eye to be tested, and 104 an objective lens. The cornea distance measuring system 100 has a first optical path 105, and a second optical path 106. The first optical path 105 generally comprises a two-dimensional image sensor 107 acting as a second light receiving portion, an imaging lens 108, a half mirror 109, a diaphragm 110, a lens 111, a total reflecting mirror 112, a lens 113, a half mirror 114, a dichroic mirror 115, and an objective lens 104. The second optical path 106 generally comprises a half mirror 116, a lens 117, total reflection mirrors 118, 119, and a diaphragm 124.

The ring-shaped light source projecting portion 102 comprises a ring-shaped light source and a pattern plate (not shown). In this embodiment, although an illumination light, which is parallel in rays of light in meridional section, is projected to the eye, a radiating illumination light may be projected to the eye. When this illumination light is irradiated toward the eye 103, a ring-shaped virtual image 121 is formed on a cornea 120 of the eye 103. In this embodiment, the wavelength of the illumination light of the ring-shaped light projecting portion 102 is 900 nm to 1000 nm. The dichroic mirror 115 has a role for transmitting the illumination light and reflecting a wavelength of a near infrared light.

Figure 2:
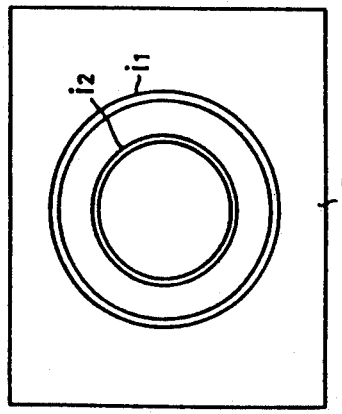

A reflected light by the cornea 120 is guided to the half mirror 114 through the objective lens 104 and dichroic mirror 115 and branched to the first and second optical paths 105 and 106. The reflected light guided to the first optical path 105 is once imaged as a ring-shaped aerial image 122 through the lens 113 and then imaged as a ring image $i_2$ (see FIG. 2) on the two-dimensional image sensor 107 via the total reflection mirror 112, lens 111, diaphragm 110, half mirror 109 and imaging lens 108. The imaging power of this ring image $i_2$ is 0.5 times in this embodiment. The reflected light guided to the second optical path 106 is reflected by the total reflection mirror 119, then once imaged as an air image 123 through the objective lens 104 and then imaged on the two-dimensional image sensor 107 as a ring image $i_1$ through the total reflection mirror 118, lens 117, half mirror 116, diaphragm 124, half mirror 109, and imaging lens 108. The imaging power of this ring image $i_1$ is set to be larger than the imaging power of the ring image $i_2$.

The diaphragm 110 has a role for acting as a second diaphragm and is relayed to the neighborhood of the focusing position behind the objective lens 104 by the lens 113 and a conjugate 125 is formed at the focusing position therebehind. The optical system of the first optical path 105 is generally telecentric toward the object side. The diaphragm 124 has a role for acting as a first diaphragm and is relayed to the forward of the testing eye 103 by the lens 117. And a conjugate image (real image) 126 is formed in a position 25 mm to 50 mm away forwardly from the eye here.

Figure 3:
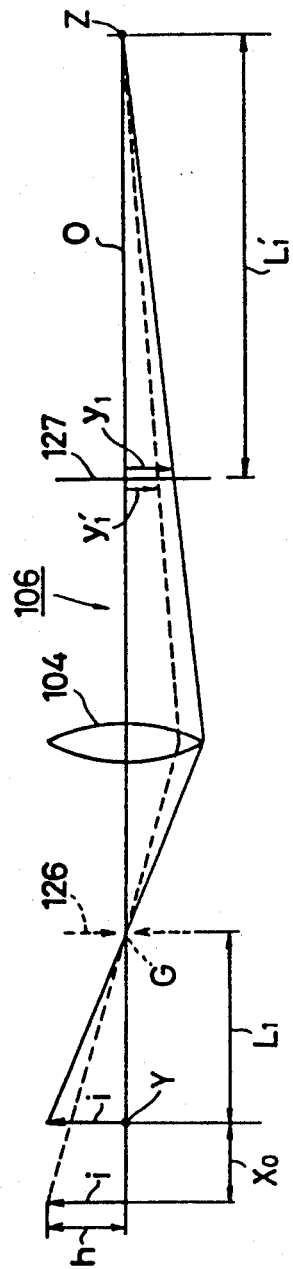
Figure 4:
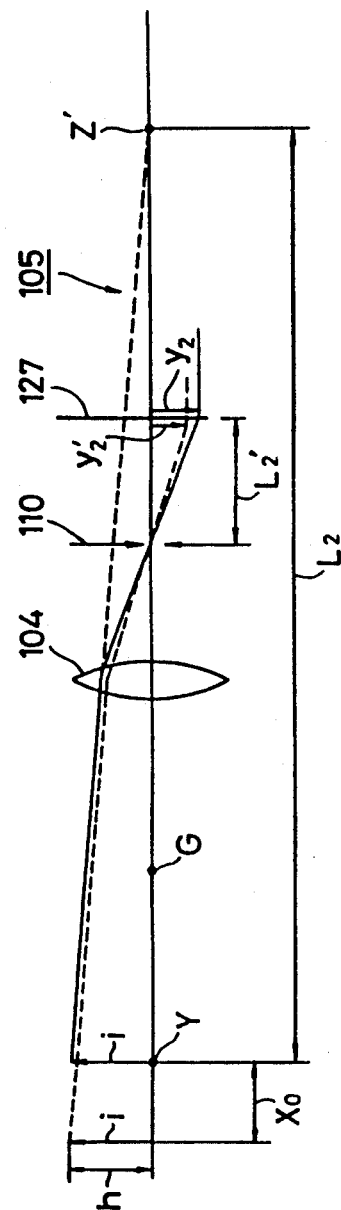

This embodiment will be described in more detail with reference to FIGS. 3 and 4 which schematically show a relation between the objective lens 104 and the diaphragms 110, 124. In this embodiment, an origin G is set to one point on an optical axis O where the conjugate image 126 of the diaphragm 124 is formed, and a reference position Y is set to a position away in the direction of the optical axis O from the origin G by a distance $L_1$. The location of this reference position Y is deliberately determined so that the ring images $i_1$ and $i_2$ are not defocused. An object having a height h (this height is equal to the radius of the ring image i) is placed at this reference position Y. The height of an image formed on an observing plane 127 (position where the two-dimensional image sensor 107 is located) by the second optical path 106 at this time is represented by $y_1$ and the height of another image formed on the observing plane 127 by the first optical path 105 is represented by $y_2$. Then, this known object is moved by a distance $X_0$ and the heights of the images in these new positions are represented by $y_1'$ and $y_2'$, respectively. Further, a distance from the observing plane 127 to a point Z is represented by $L_1'$, a distance from the reference position Y to a point Z' is represented by $L_2$, and a distance from the diaphragm 110 to the observing plane 127 is represented by $L_2'$. Furthermore, a magnifying power for relaying the diaphragm 126 to the point Z is represented by $\beta_1$ and a magnifying power for relaying the diaphragm 110 to the point Z' is likewise represented by $\beta_2$.

Then, the following relations can be obtained.

$$h/L_1 = y_1 \cdot \beta_1 / L_1' \qquad (1)$$

$$h/(L_1 + X_0) = (y_1' \cdot \beta_1)/L_1' \qquad (2)$$

$$h/L_2 = y_2/(\beta_2 \cdot L_2') \qquad (3)$$

$$h/(L_2 + X_0) = y_2'/(\beta_2 \cdot L_2') \qquad (4)$$

Presuming that the magnifying power $\beta_1$, and the distances $L_1$, $L_1'$ are all constant in the above-mentioned relations (1) and (2), if the following replacement is made, $$K_1 = (\beta_1 \cdot L_1)/L_1'$$

$$K_2 = \beta_1 / L_1'$$

then the relations (1) and (2) are rewritten as follows;

$$h = K_1 \cdot y_1 \qquad (5)$$

$$h = K_1 \cdot y_1' + K_2 \cdot y_1' \cdot X_0 \qquad (6)$$

Likewise, presuming that the magnifying power $\beta_2$, and the distances $L_2$, $L_2'$ are all constant in the above-mentioned relations (3) and (4), if the following replacement is made, $$K_3 = L_2/(L_2' \cdot \beta_2)$$

$$K_4 = 1/(L_2' \cdot \beta_2)$$

then the relations ③ and ④ are rewritten as follows;

$$h = K_3 \cdot y_2 \quad (7)$$

$$h = K_3 \cdot y_2' + K_4 y_2' \cdot X_0 \quad (8)$$

Now, the constants $K_1$, $K_2$, $K_3$ and $K_4$ can be determined by actually measuring the height h of the object and the height y of the image.

That is, by rewriting the relations ⑤ and ⑥, the following relations can be obtained.

$$K_1 = h/y_1 \quad (9)$$

$$K_2 = (h/y_1)(y_1 - y_1')/(y_1' \cdot X_0) \quad (10)$$

$$K_3 = h/y_2 \quad (11)$$

$$K_4 = (h/y_2)(y_2 - y_2')/(y_2' \cdot X_0) \quad (12)$$

Thus, by actually measuring the height h of a known object as well as the height of its image, the contacts $K_1$, $K_2$, $K_3$ and $K_4$ are obtained.

Next, there will be described how the measurement is carried out when the height h of an object and the distance X from the reference position Y are unknown.

In this case, a distance X is substituted for the distance $X_0$ in the above-mentioned relations ② and ④. Further, $y_1$ and $y_2$ are substituted for $y_1'$ and $y_2'$.

Then, the following relations are obtained.

$$h = k_1 \cdot y_1 + K_2 \cdot y_1 \cdot X \quad (14)$$

$$h = K_3 \cdot y_2 + K_4 \cdot y_2 \cdot X \quad (15)$$

If the above simultaneous equations are simultaneously solved for the distance X and the height h of the object, the following answers can be obtained.

$$X = (K_3 \cdot y_2 - K_1 \cdot y_1)/(K_2 \cdot y_1 - K_4 \cdot y_2) \quad (16)$$

$$h = K_1 \cdot y_1 + K_2 \cdot y_1 \cdot X \quad (17)$$

$$= (K_2 \cdot K_3 - K_1 \cdot K_4) y_1 \cdot y_2/(K_2 \cdot y_1 - K_4 \cdot y_2)$$

Therefore, by measuring the image heights $y_1$ and $y_2$, the distance from the object from the reference position Y can be measured.

Next, the measurements of the radius R of curvature of a cornea and the position of its vertex will be described with reference to FIG. 5.

Figure 5:
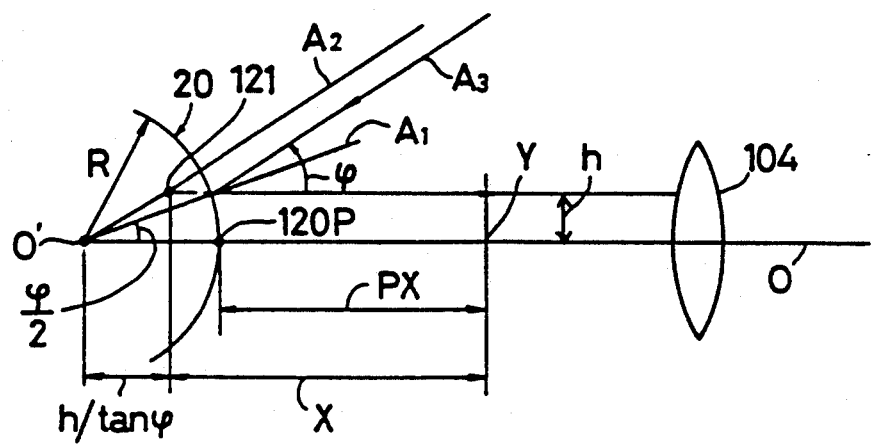

In FIG. 5, the radius (the long diameter or the short diameter when it resembles an ellipse) of a ring image i is presumed to be the height h of the object. At this time, the object height h is determined by a meridional ray. If the diameter of the ring image is approximately 3 mm, the angle $\phi$ becomes approximately 20°, and the under-listed paraxial calculating equation cannot be used.

$$h = (R \cdot \sin \phi)/2$$

Therefore, if the distance $L_2$ is set to be large enough, the angle $\phi$ is normally held to be constant and one measured by the second optical path 106 passing the diaphragm 124 is used as the object height h, an equation based on the underlisted reflexive law can be used.

$$h = R \cdot \sin (\phi/2)$$

If the above equation is rewritten, the following equation is obtained.

$$R = h/\sin (\phi/2) \quad (18)$$

Presuming that the distance $L_1$ is set such that an angle between light beams passing the diaphragms 110 and 124 does not become large excessively, if the object height h obtained by the equation 17 is substituted into the above-mentioned equation 18 and if the position of the corneal vertex is presumed to be a distance $P_x$, the following equation can be obtained.

$$P_x = X - (R - h/\tan \phi) \quad (19)$$

The equation 19 for the position of the corneal vertex is presumed to require the presence of the ring image on the optical path of the spherical surface. And it is subject to an influence of spherical aberration. However, the influence is supposedly not decisive and accordingly it can be amended based on experimental data.

In FIG. 5, O' represents the center of curvature of the cornea, $A_1$ represents a normal line, $A_2$ represents a spherical optical axis when the cornea 120 is regarded as a spherical surface, and $A_3$ represents an incident ray to the cornea 120.

Next, the interference optical system will be described with reference to FIG. 1.

The interference optical system 101 includes a laser diode 130, a lens 131, a pin hole 132, a beam splitter 133, a lens 134, a focusing lens 135, a total reflection mirror 136, a lens 137, total reflection mirrors 138, 139 and 140, a model eye unit member 141, a total reflection mirror 142, a pin hole 143, a lens 144, and a photosensor 145 having a point aperture. The laser diode 130 is of a low coherent length. The coherent length is, for example, approximately 0.05 mm to 0.1 mm. The wavelength is near infrared and has an effect for preventing dazzling. A laser beam emitted from the laser diode 130 is condensed to the pin hole 132 by the lens 131. The pin hole 132 has a role for acting as a secondary point-like source of light. Instead of the laser diode, an LED having a narrow spectral width may be used as a light source.

A laser beam transmitted through the pin hole 132 is split into a light beam proceeding to the lens 134 and another light beam proceeding to the lens 137 by the beam splitter 133. The lens 134 constitutes a measuring optical path 130' together with the lens 135, total reflection mirror 136, and dichroic mirror 115. The other lens 137 constitutes a reference optical path 140' together with the total reflection mirrors 138, 139 and 140 and model eye unit member 141.

Each of the lenses 134 and 137 has a role for collimating the laser beam transmitted through the pin hole 132. The laser beam collimated by the lens 134 is caused to form a spot at a focusing position 146 by the focusing lens 135. This focusing lens 146 is conjugate with an eye fundus 147 with respect to the objective lens 104. The laser beam for forming a spot at the focusing position 146 is guided to the testing eye 103 via the total reflection mirror 136, dichroic mirror 115, and objective lens 104, and forms a spot on the fundus 147. Since the fundus 147 and the focusing position 146 are conjugate with each other with respect to the objective lens 104 in this embodiment, even if the an optical axis (optical axis O of the objective lens) of the measuring instrument is not coaxial with an optical axis of the testing eye 103, a reflected light from the fundus 147 forms an image at the focusing position 146.

The pin hole 143 is formed at the focusing position of the lens 134 and is conjugate with the fundus 147. The lens 135 has a role for collimating the reflected light from the fundus 147 and such collimated light is relayed to the pin hole 143 via the beam splitter 133 and the total reflection mirror 142 by the lens 134. The pin hole 143 becomes conjugate with the pin hole 132 with respect to a reflecting surface of the beam splitter 133. Further, since the pin hole 132 and the spot light 147 on the fundus are conjugate with each other, even if the alignment of the measuring instrument is slightly deviated with respect to the testing eye, the reflected light from the fundus 147 can transmit through the pin hole 143.

The laser beam collimated by the lens 137 is guided to the model eye unit member 141 by the mirrors 138, 139 and 140. The model eye unit member 141 is movable so that the optical path length of the reference optical path and the optical path length of the measuring optical path become the same. This model eye unit member 141 generally comprises a lens 148, a reflecting mirror 149, and a movable framework 150. This model eye unit member 141 is used in order to obviate possible deflection of the reflected light beam owing to blur caused by movement thereof, and a movable mirror may be used without any technical difference in effect in principle.

Figure 6:
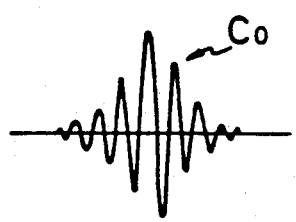

The reflected light from the fundus and the reference light are condensed to the pin hole 143, and the light beam transmitted through the pin hole 143 is converged to a photosensor 145 as a first light receiving portion by the lens 144. When the difference in optical path between the reference optical path and the measuring optical path becomes about the coherent length of the laser diode 130 as a result of the movement of the model eye unit member 141, an interference waveform shown in FIG. 6 can be obtained. The interference waveform is changed like a sine-wave every time the wavelength is changed.

Presuming now that the coherent length of the laser diode 130 is 0.1 mm, the interference occurable position can be determined with a portion of resolving power, and thus it can be favorably used for the measurement of the length of eye axis.

The measurement of the length of the eye axis, if the movement of the testing eye is taken into consideration, is preferably carried out in such a manner as that the determination of the position of the corneal vertex 120P and the determination of the interference position are simultaneously performed. In view of the above, if, for example, it is constructed such that the model eye unit member 141 is activated and the ring images $i_1$ and $i_2$ formed on the two-dimensional image sensor 107 are stored in a frame memory immediately after the photosensor 145 outputs the maximum amplitude waveform (peak), the time-wise deviation can be restrained to about one thirtieth even if the deviation is the largest and thus, desirable.

A signal processing circuit of the interference optical system and cornea position detection system will now be described.

Figure 10:
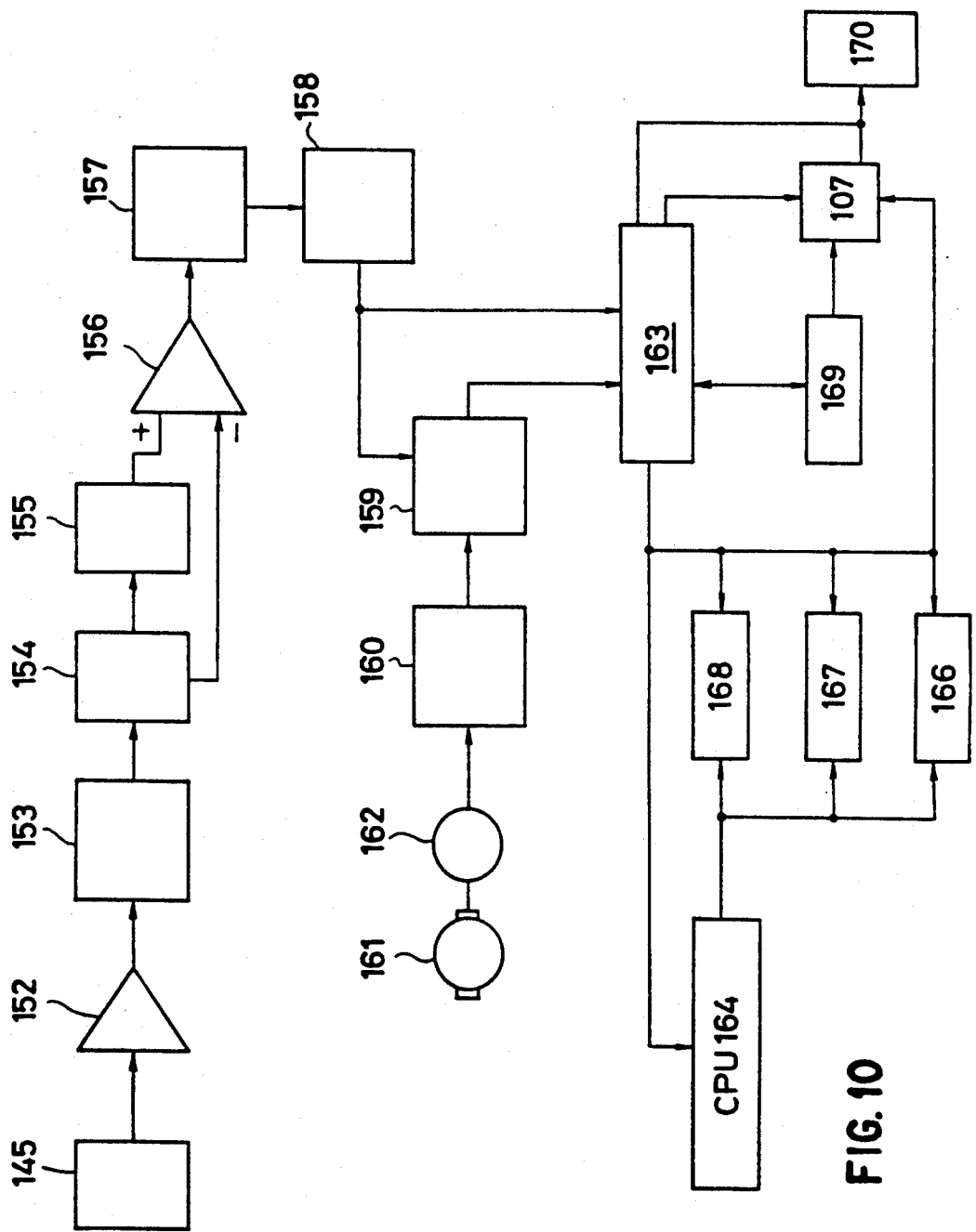

FIG. 10 is a block diagram of a signal processing circuit of the interference optical system and cornea position detection system.

Figure 7:
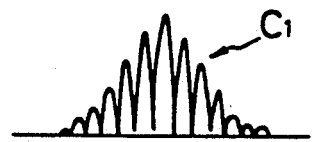
Figure 8:
Figure 9:
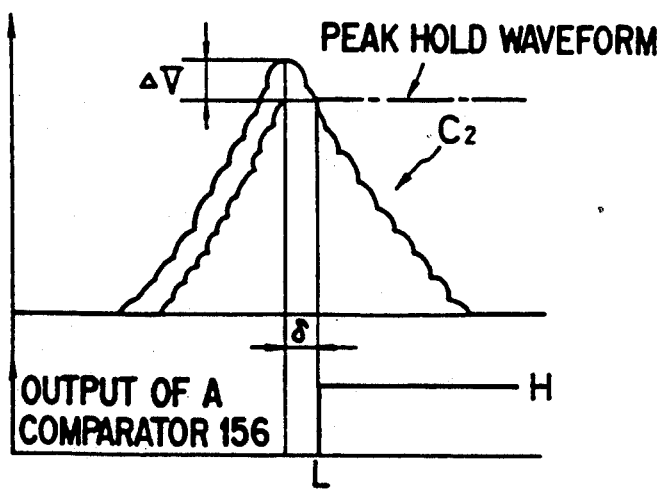

The output of the photosensor 145 is input into a fullwave rectification circuit 153 through a preamplifier 152, and an amplified output of the preamplifier 152 is rectified to a full-wave rectification waveform $c_1$ shown in FIG. 7 by the full-wave rectification circuit 153. The full-wave rectification waveform $c_1$ is input into a smoothing circuit 154 and converted to a smooth wave $c_2$ shown in FIG. 8. The smooth wave $c_2$ is input into a plus terminal of a comparator 156 through a hold circuit 155 and directly input into a minus terminal of the comparator 156. The hold circuit 155 has such a function here as to hold a voltage which is lower than the output voltage of the smoothing circuit 154 by $\Delta V$ as shown in FIG. 9. Accordingly, when the voltage of the smooth wave $c_2$ becomes lower than the hold voltage, the output of the comparator 156 is brought to H from L. Presuming here that the smooth waveform $c_2$ is sufficiently high in speed and the $\Delta V$ is extremely small, a deviation $\delta$ of the peak position also becomes small and it may think that it shows a peak.

The output of the comparator 156 is input into a latch circuit 159 through a chattering remove circuit 157 and a waveform rectification circuit 158. The latch circuit 159 has such a role as to latch a count data of a counter 160 in accordance with the movement of the model eye unit member 141. That is, the counter 160 has a pulse output which is input therein from an encoder 162 which is rotated in accordance with rotation of a motor 161, and the number of its pulse corresponds to the moving amount of the model eye unit member 141.

Therefore, the latch circuit 159 is operated to latch the data on a moving position of the model eye unit member 141 when a peak of the interference waveform $c_0$ is obtained, and the data on the moving position is input into a CPU 164 through an input-output circuit 163 and a distance from the measuring instrument to the fundus 147 is calculated at a real time. Simultaneously, the output of the waveform rectification circuit 158 is input into the two-dimensional image sensor 107 through the input-output circuit 163, and data on the ring images $i_1$ and $i_2$ formed on the two-dimensional image sensor 107 are stored in a frame memory 166, the position of the corneal vertex 120P being detected on a basis of the date stored in the frame memory 166. Since the operation thereof is already described above, no further description will be made.

The numeral 167 denotes a RAM, and the numeral 168 denotes a ROM, data, etc. stored therein being used in accordance with necessity. Similarly, the numeral 169 denotes a gate array which is used when data of the two-dimensional image sensor 107 is taken out, and the numeral 170 denotes a monitoring TV on which besides the length of the eye axis, the ring images $i_1$ and $i_2$ are shown together with an image of the anterior portion in accordance with necessity.

The determination of the length of the eye axis is made based on the following equation.

Figure 11:
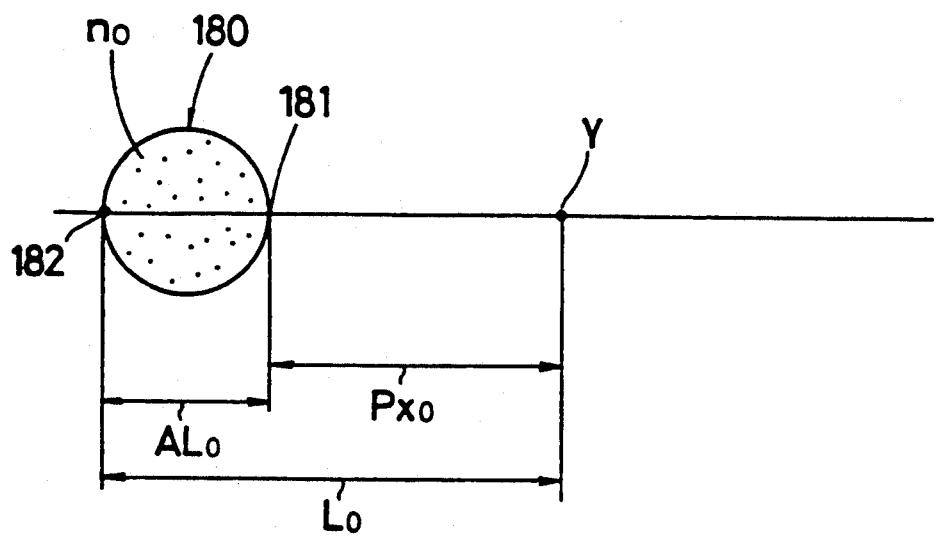
Figure 12:
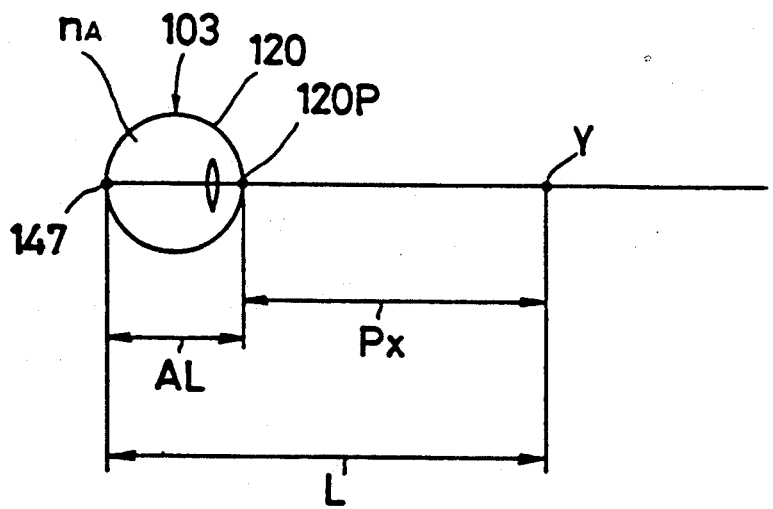

Regarding a model eye 180 having a known eye axis length $AL_0$ which is placed in a predetermined position as shown in FIG. 11, a distance from the reference position to a corneal vertex 181 is represented by $P_{x0}$. At this time, the position of the model eye unit member 141 when a peak of the interference waveform occurs is set to $m_x = 0$. If an optical path length from an imaginary reference position Y to a fundus 182 is represented by $L_0$ and the refractive index of the model eye 180 is represented by $n_0$, the following equation can be obtained.

$$L_0 = n_0 \cdot AL_0 + P_{x0}$$

Next, if an unknown average refractive index of the testing eye 103 is represented by $n_A$, the eye axis length is represented by AL and a distance from the reference position Y to the corneal vertex 120P is represented by $P_x$, the following equation can be obtained.

$$m_x = L - L_0$$
$$= n_A \cdot AL - n_0 \cdot AL_0 + P_x - P_{x0}$$

Thus, it can be rewritten as follows.

$$AL = (m_x + P_{x0} - P_x + n_0 \cdot AL_0)/n_A$$

Therefore, the eye axis length AL can be found using the above-mentioned calculation formula.

Therefore, the signal processing circuit functions as a fundus position measuring portion and a cornea position measuring portion.

In the signal processing circuit according to the present invention, since the data on the corneal vertex position can be taken into the frame memory at a real time simultaneously with the measurement of the fundus position, measuring accuracy of the eye axis length can be enhanced when compared with such a stepping measurement case as that the corneal vertex position is found first and then the fundus position is found.

Although the first embodiment has been described in the foregoing, the beam splitter 133 shown in FIG. 1 is desirably designed such that the transmittance thereof is made as small as possible and the reflective index thereof is made large. The reason is as follows. Since the light quantity irradiated to the fundus 147 is limited in view of safety, in order to enhance the efficiency of the photosensor 145, there is no other way but to guide as much reflected light from the fundus as possible is guided to the photosensor 145. Although the reference light is large in quantity compared with the reflected light from the fundus, if the dynamic range of the photosensor 145 is arranged to be large and only an alternating current component is taken off, noise component, etc. caused by dark current of the photosensor 145 can be removed.

Further, since the quantity of light made incident to the photosensor 145 is abruptly reduced when the focusing position relative to the retina is deviated, it may be designed such that by serving the reflection mirror 142 as a quick return mirror, the reflected light is caused to pass through the lens 151, mirrors 116, 109, and lens 108 and formed into a spot image on the two-dimensional image sensor 107 together with an image of the anterior portion so that they can be observed. In this case, a short pass filter is used instead of the total reflection mirror 116.

According to the first embodiment, since it is intended to measure the position of the corneal vertex using a double ring image, the radius of curvature of the cornea can be measured in the first place. Accordingly, it can also be used as a corneal configuration measuring apparatus (kerato apparatus).

Second Embodiment 2

Figure 13:
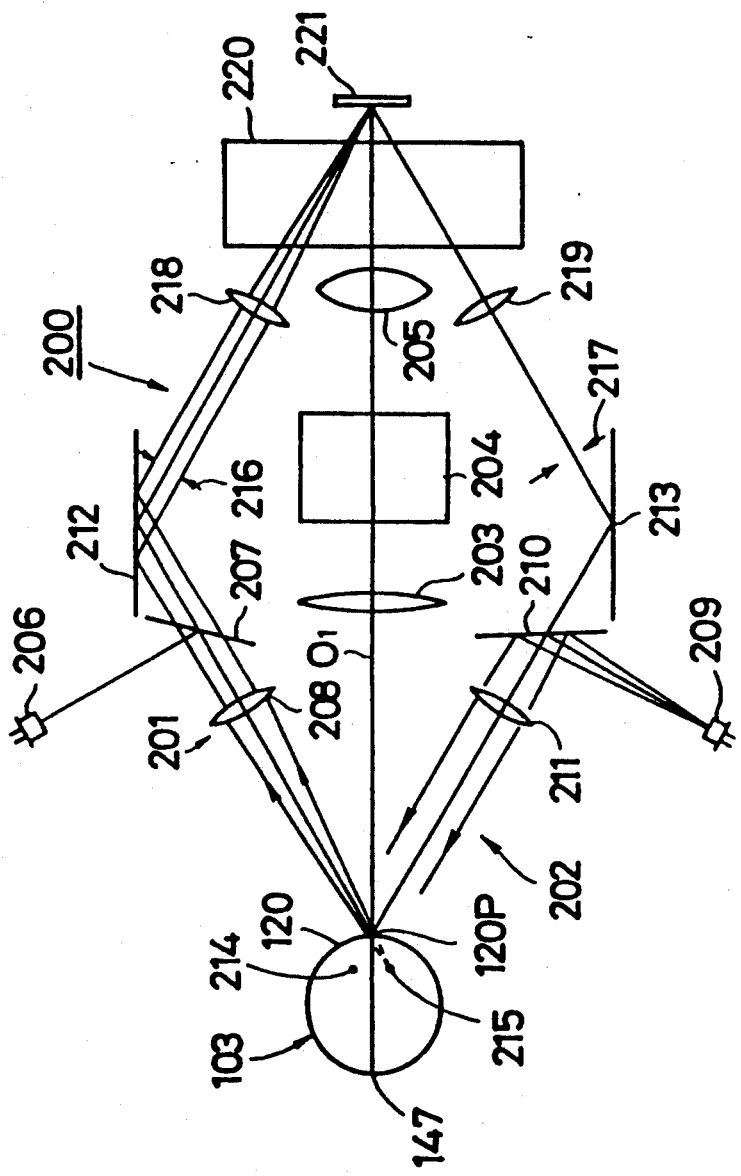
FIGS. 13 through 19 show an intraocular length measuring instrument according to a second embodiment of the present invention.

FIG. 13 shows an optical system for finding a corneal vertex position using an alignment optical system as a cornea distance measuring system.

In FIG. 13, the alignment optical system 200 comprises a first optical system 201 and a second optical system 202. The first and second optical systems 201 and 202 are symmetric with respect to an optical axis $O_1$. An objective lens 203, a mirror 204 and an imaging lens 205 are disposed on the optical axis $O_1$. The objective lens 203 and the imaging lens 205 are used for observing the anterior portion of the testing eye 103. A half mirror or a band pass mirror is used as the mirror 204. The mirror 204 has a role for reflecting a laser beam when a measurement is made using an interference optical system shown in FIGS. 14 and 15. The construction of this interference optical system will be described later.

The first optical system 201 includes, as a light irradiation optical system, a point light source 206, a half mirror 207, and a lens 208, whereas the second optical system 202 includes, as a light irradiation optical system, a point light source 209, a half mirror 209, and a lens 211. The point light source 206 is located in a focusing position of the lens 208 through the half mirror 207, whereas the point light source 209 is located in a focusing position of the lens 211 through the half mirror 210. The light emitted from the point light source 206 is projected to the cornea 120 of the testing eye 103 in the form of parallel beams of light by the lens 208, whereas the light emitted from the point light source 209 is projected to the cornea 120 in the form of parallel beams of light by the lens 211.

The parallel light beam made by the lens 211 is reflected on the outer surface of the cornea 120, and the reflected light beam is guided to a total reflection mirror 212 after passing through the lens 208 and half mirror 207. On the other hand, the parallel light beam made by the lens 208 is reflected on the outer surface of the cornea 120 as a divergent light from the focusing position of the cornea, and the reflected light beam is guided to a total reflection mirror 213 after passing through the lens 211 and half mirror 210 and is reflected by this total reflection mirror 213. By this specular reflection of the cornea, point luminous images 214 and 215 are formed on the cornea 120 based on the point light sources 206 and 209.

On the object side in front of the reflecting direction of the total reflecting mirror 212, a telecentric diaphragm 216 is placed. Likewise, another telecentric diaphragm 217 is placed on the object side in front of the reflecting direction of the total reflection mirror 213. The telecentric diaphragms are placed in rear focal points of the lenses 208 and 211. In this embodiment, the lens 208, total reflection mirror 212, and diaphragm 216 (lens 211, total reflection mirror 213 and diaphragm 217) constitute a light receiving optical system. The reflected light from the total reflection mirrors 212 and 213 are guided to the lenses 218 and 219 after passing through the diaphragms 216 and 217. The diaphragms are conjugate with an image sensor 221 with respect to the lenses 218 and 219, whereas the diaphragms 216 and 217 are placed in the focal points of the lenses 218 and 219. The lenses 218 and 219 are telecentrically placed on the image side. The reflected light guided to the lenses 218 and 219 are respectively imaged on a two-dimensional image sensor 221 as a second light receiving portion after passing through a mirror 220.

Figure 18:
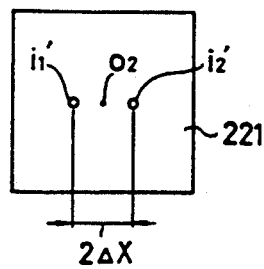
Figure 16:
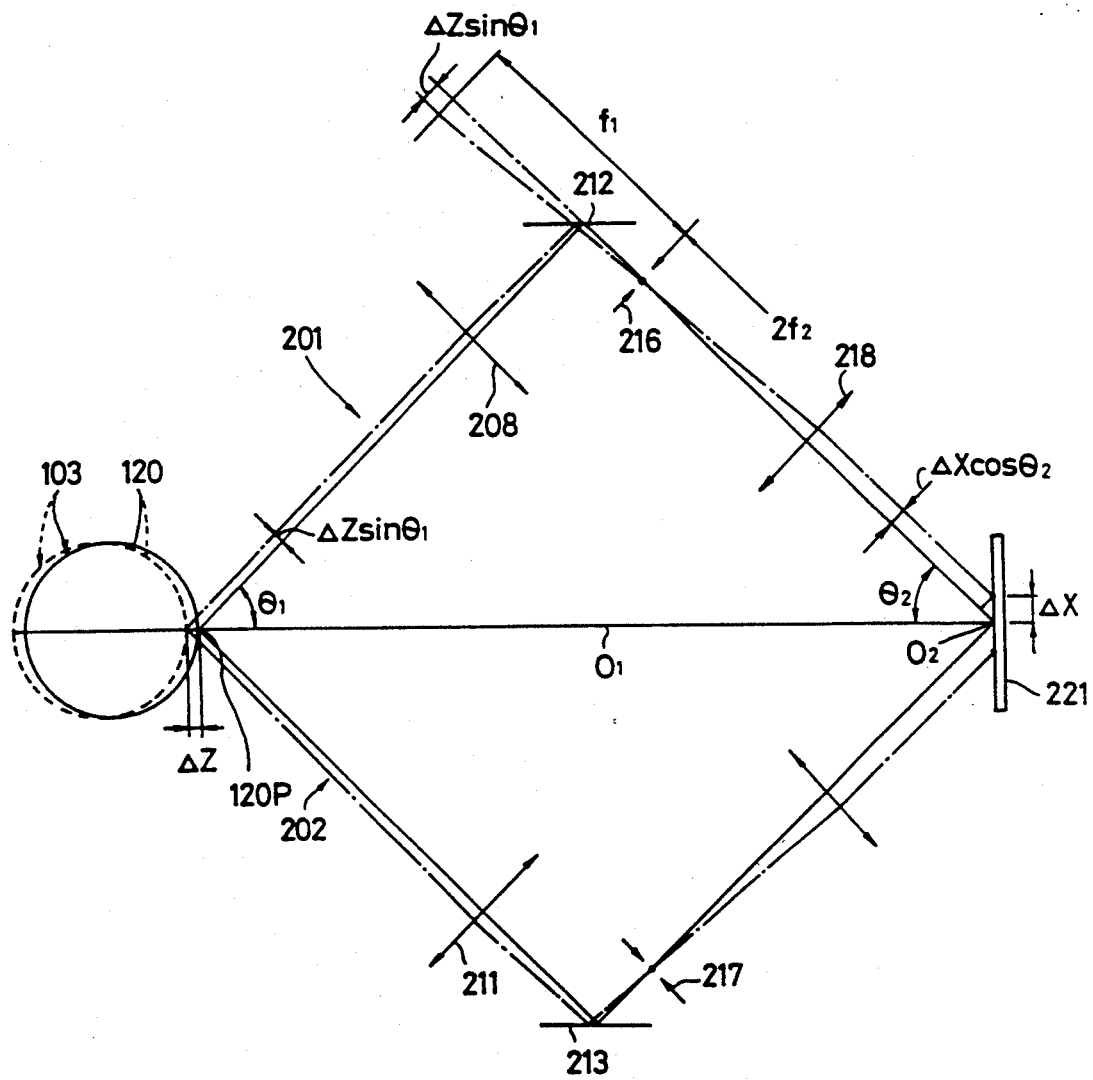
Figure 17:
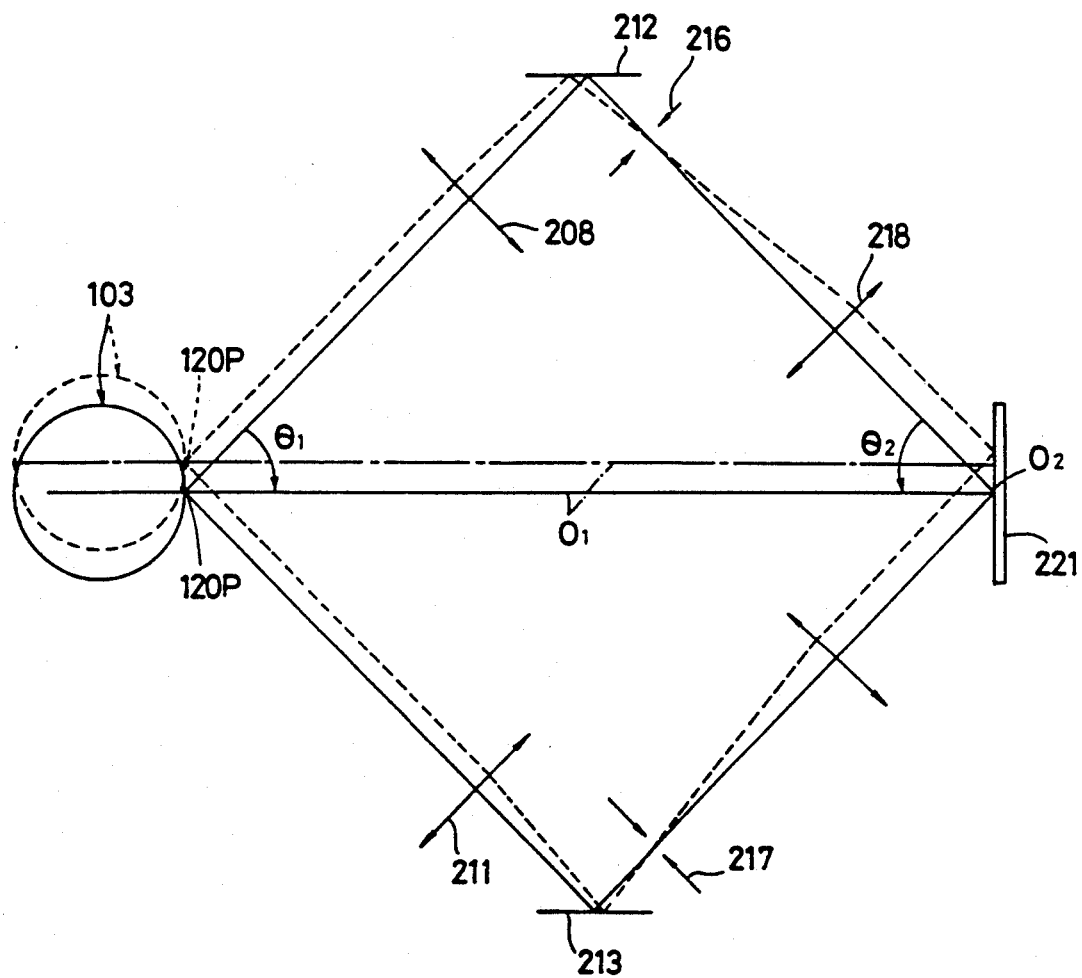

According to this alignment optical system 200, as shown in FIG. 16, even where the working distance of the measuring instrument is displaced in the direction of the optical axis with respect to the testing eye 103, an angle $\theta_1$ formed between an optical axis $O_1$ and a principal ray of the alignment optical system 200 on the object side is equal to an angle $\theta_1$ formed between an optical axis $O_1$ and a principal ray of the alignment optical system 200 when the working distance is not displaced. Likewise, an angle $\theta_2$ formed between the optical axis $O_1$ and the principal ray of the alignment optical system 200 on the image side is equal to an angle $\theta_2$ formed between the optical axis $O_1$ and the principal ray of the alignment optical system 200 when the working distance is not displaced. Further, on the two-dimensional image sensors 221, luminous point images $i_1'$ and $i_2'$, as shown in FIG. 18, are splitly formed in symmetrical positions with reference to the center $O_2$. On the other hand, although the working distance is coincident with the corneal vertex 120P, where the alignment of the measuring instrument is deviated either rightward or leftward with respect to the testing eye 103, as shown in FIG. 17, an angle $\theta_1$ formed between the optical axis $O_1$ and the principal ray of the alignment optical system 200 on the object side is equal to an angle $\theta_1$ formed between the optical axis $O_1$ and the principal ray of the alignment optical system 200 when the working distance is not displaced. Likewise, an angle $\theta_2$ formed between the optical axis $O_1$ and the principal ray of the alignment optical system 200 on the image side is equal to an angle $\theta_2$ formed between the optical axis $O_1$ and the principal ray of the alignment optical system 200 when the working distance is not displaced. In this case, the luminous point images $i_1$ and $i_2$ are not separated and their positions are displaced from the origin $O_2$ of the two-dimensional image sensor 221.

In this embodiment, the focal length of the lens 208 is represented by $f_1$ and the focal length of the lens 218 is represented by $f_2$. Further, the diaphragm 216 is considered to be a reference. In FIG. 16, when the working distance is displaced by $\Delta Z$, the position of the principal ray is displaced by $\Delta Z \cdot \sin\theta_1$ compared with a case where the working distance is not displaced. Furthermore, since the optical system constituted by the lens 208, diaphragm 216 and lens 218 is telecentric toward the object and image as shown in FIG. 16, the displacement $\Delta Z$ of the working distance is in a proportional relation with a distance $\Delta X$ from the center $O_2$ on the two-dimensional image sensor 221 to the luminous point $i_1'$ or $i_2'$.

Accordingly, if the magnifying power of this optical system is represented by $\beta$, the following equation can be obtained.

$$\Delta Z \sin\theta_1 = \beta \cdot \Delta X \cos\theta_2$$

Since the magnifying power $\beta$ satisfies the following equation here, $$\beta = f_2/f_1$$

the displacement $\Delta Z$ of the working distance can be expressed as follows;

$$\Delta Z = \frac{f_2}{f_1} \cdot \frac{\cos\theta_2}{\sin\theta_1} \cdot \Delta X$$

Hereby, it is defined such that $\Delta X$ is positive when the luminous point image $i_1$ is located at a right-hand side of the luminous point image $i_2$, and that $\Delta X$ is negative when the condition is reverse.

By the way, since the luminous point images $i_1'$ and $i_2'$ are not something which can be particularly distinguished, it is impossible to distinguish them when the luminous point images $i_1'$ and $i_2'$ are simultaneously formed on the two-dimensional image sensor 221. Even if it is possible, when they are gradually overlapped, it becomes impossible to find their positions correctly. Accordingly, the point light source 206 corresponding to the luminous point image $i_1'$ is illuminated, an image data of the two-dimensional image sensor 221 of the luminous point image $i_1$ is accumulated in a frame memory, then the point light source 209 corresponding to the luminous point image $i_2'$ is illuminated, an image data of the luminous point image $i_2'$ is accumulated in a frame memory, and the distance between these luminous point images $i_1'$ and $i_2'$ are found based on this image data. If a distance $2\Delta X$ between the luminous point images of the two dimensional image sensor 221 is measured, since $f_1$, $f_2$, $\theta_1$ and $\theta_2$ are known, displacement $\Delta Z$ of the working distance can be obtained, and the distance from the corneal vertex 120P to the reference position of the measuring instrument can be obtained.

Figure 19:
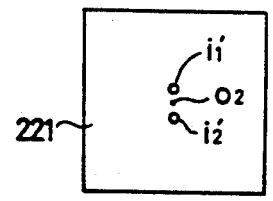

If the lens 218 is slightly displaced upwardly in the direction perpendicular to a paper surface and the other lens 219 is displaced downwardly in the direction perpendicular to a paper surface, since the luminous point images $i_1'$ and $i_2'$, as shown in FIG. 19, are formed on the two-dimensional image sensor 221 in such a state as being split in the vertical direction when the working distance is predetermined, the measurement can also be carried out in a state wherein the point light sources 206 and 209 are simultaneously lighted up. However, if this situation is more strictly viewed, since the principal rays of the luminous point images $i_1'$ and $i_2'$ are displaced from a plane vertical to an observing plane of the two-dimensional image sensor 221, the relation between $\Delta X$ and $\Delta Y$ is slightly displaced. However, an error based on its effect is so small that it can be disregarded.

The construction of an interference optical system 250 will not be described with reference to FIGS. 14 and 15.

Figure 14:
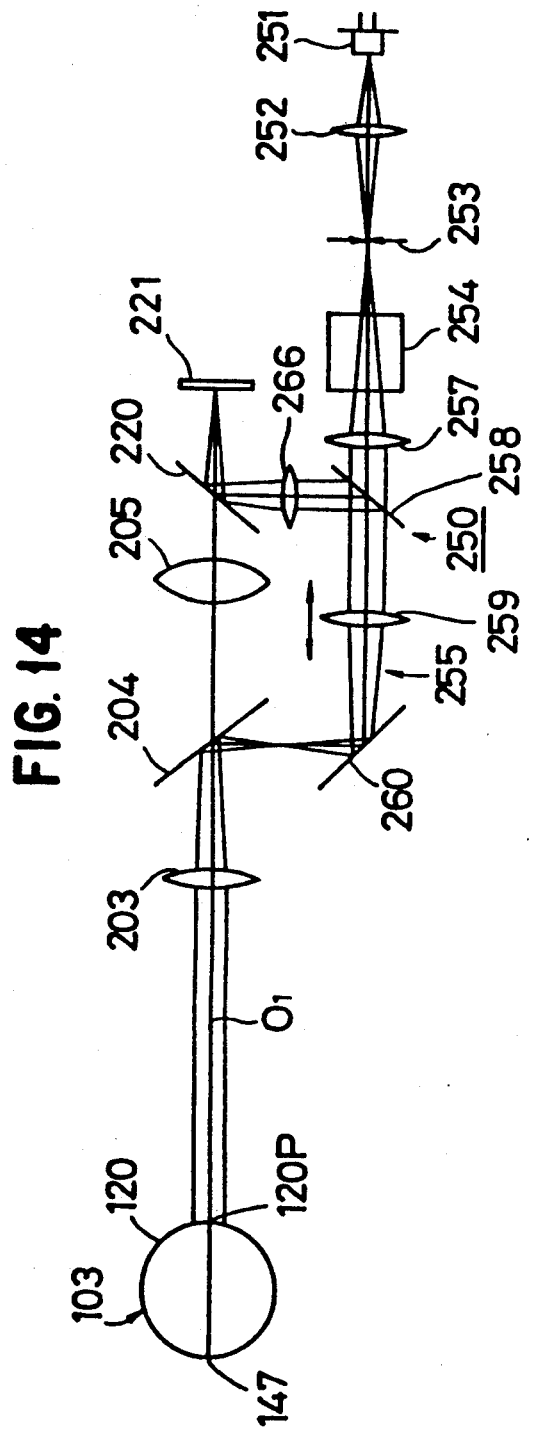
Figure 15:
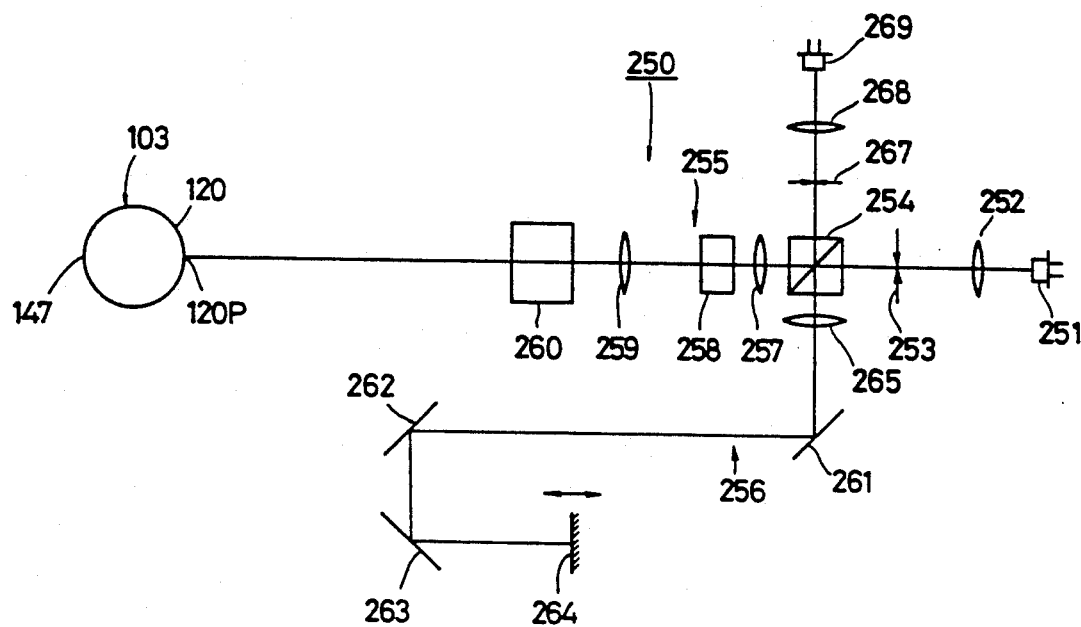

The interference optical system 250, as shown in FIG. 14, includes a laser diode 251, a lens 252, a pin hole 253, and beam splitter 254. As for the laser diode 251, one having a low coherent length as in the first embodiment is used. The laser beam emitted from the laser diode 251 is condensed to the pin hole 253 by the lens 252. The pin hole 253 has a role for acting as a secondary light source. The laser beam passed through the pin hole 253 is split by the beam splitter 254. The beam splitter 254 has such a function as to split the laser beam into a measuring light and a reference light. In FIG. 15, the numeral 255 denotes a measuring optical path, and the numeral 256 denotes a reference optical path.

The measuring optical path 255 is provided with a lens 257, a half mirror 258, a lens 259, and a total reflection mirror 260. The reference optical path 256 is provided with total reflection mirrors 261, 262 and 263, a movable mirror 264, and a lens 265. The pin hole 253 is formed in the focusing positions of the lenses 257 and 265. The measuring beam of light is converted to a parallel beam of light by the lens 257 and then projected to the fundus 147 of the testing eye 103 after passing through the half mirror 258, lens 259, total reflection mirror 260, half mirror 204 and objective lens 203. The reflected light beam from the eye fundus 147 is guided to the half mirror 258 via the lens 203, half mirror 204, total reflection mirror 260 and lens 259. And a part of the reflected light beam is reflected by this half mirror 258 and imaged on the two-dimensional image sensor 221 through the half mirror 220. The light beam reflected from the eye fundus and passed through the half mirror 258 is guided to a pin hole 267 by the beam splitter 254. The pin hole 267 is formed in the focusing positions of the lenses 257 and 265. The reference beam of light guided to the movable mirror 264 is reflected by this movable mirror 264 and then guided to the pin hole 267 via the total reflection mirrors 263, 262 and 261, lens 265 and beam splitter 254. The reference light beam and measuring light beam that have passed this pin hole 267 are guided to a photosensor 269. By way of movement of the movable mirror 264, when an optical path difference between the reference optical path 256 and the measuring optical path 255 becomes approximately the coherent length of the laser diode 251, an interference waveform $C_0$ is output from the photosensor 269 as in the interference optical system of the first embodiment. On a basis of this interference waveform $C_0$, a distance from the reference position of the measuring instrument to the eye fundus is found, and since the position of the measuring instrument from the reference position to the corneal vertex 120P is already obtained, the eye axis length AL is found in the same manner as in the first embodiment.

Third Embodiment

Figure 20:
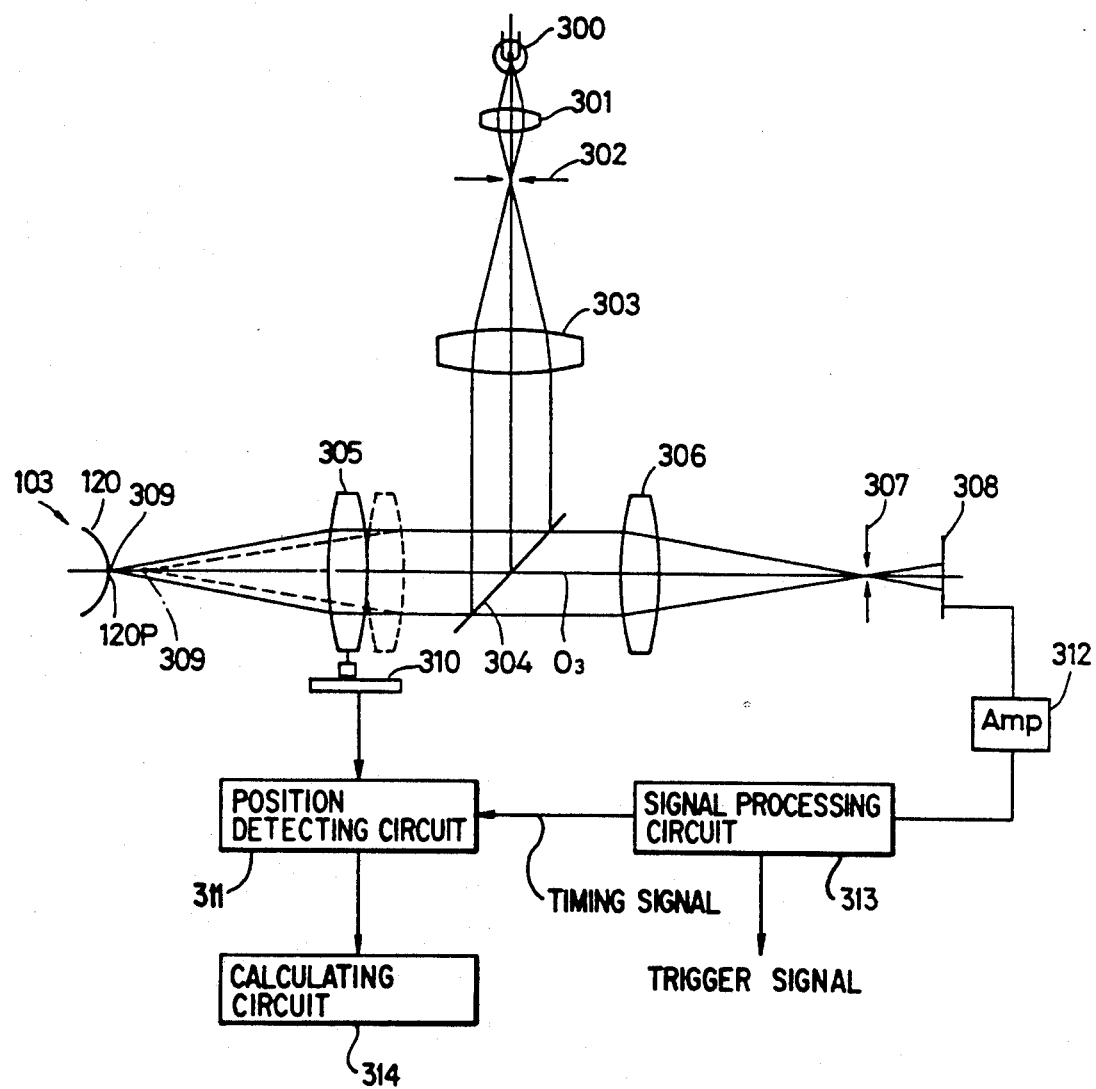

FIG. 20 shows a third embodiment in which a confocal optical system is used as a cornea distance measuring system. As for the interference optical system, since one having a similar construction to that of the first and second embodiments can be used, only the construction of the cornea distance measuring system will be described hereinafter.

The cornea distance measuring optical system comprises a light source 300, a condenser lens 301, a pin hole plate 302 as a first diaphragm, a collimate lens 303 as a relay lens, a beam splitter 304, an objective lens 305, a lens 306, a spatial filter 307, and a light receiving device 308. The light emitted from the light source 300 is condensed to the condenser lens 301 and converged to the pin hole plate 302. The pin hole plate 302 has a role for acting as a secondary light source, and the light passed through the pin hole of the pin hole plate 302 is made into a parallel beam of light by the collimate lens 303.

This parallel beam of light is reflected toward the objective lens 305 by the beam splitter 304 and then guided to the testing eye 103 as a converged light beam. The objective lens 305 has a role for geometrically converging the parallel light beam to a light converging point 309. The pin hole plate 302 and the light converging point 309 are conjugate to each other with respect to the collimate lens 303 and objective lens 305, whereas the light conversing point 309 and spatial filter 307 are conjugate with each other with respect to the lens 306. That is, the light conversing point 309 is confocal, and the cornea distance measuring system forms a confocal optical system. This confocal optical system has such an optical nature as that the light emitted from a point other than the neighborhood of the confocal point is unable to pass the spatial filter 307. The objective lens 305 has a role acting as an objective lens portion for changing the position of the condenser distribution.

The objective lens 305 is movable in the direction of the optical axis $O_3$ here, a linear encoder 310 as a position detecting mechanism faces the objective lens 305, and output of the linear encoder 310 is input into the position detecting circuit 311. The linear encoder 310 and the position detecting circuit 311 have a role for detecting the position of the objective lens 305. The output of the light receiving device 308 is input into a signal processing circuit through an amplifier 312. The signal processing circuit 313 has such a function as to output a trigger signal and a timing signal. The trigger signal is used when a laser diode (not shown) of an interference optical system is started for driving, while the timing signal is used when the lens position is specified by the position detecting circuit 311. The position detecting circuit 311 outputs a lens position detecting signal toward a calculating circuit 314. The calculating circuit 314 has a role for calculating a distance from the reference position of the measuring instrument to the corneal vertex 120P based on a distance relation between a corresponding lens position and the instrument or light light converging point 309.

Figure 21A:
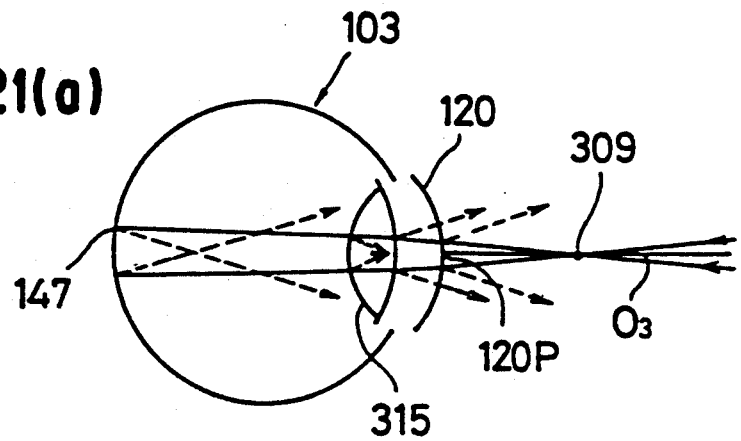
FIGS. 21(a)–21(c) are explanatory views showing changes in position of a light convergent point of the cornea distance measuring system.
Figure 21B:
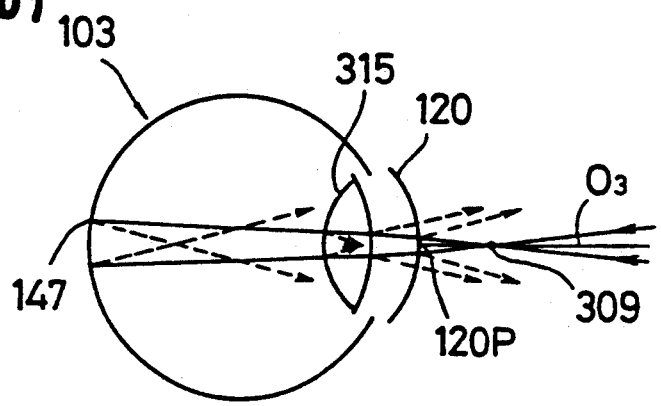
Figure 21C:
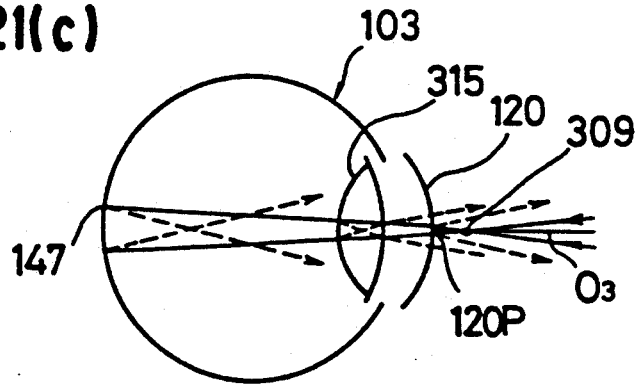

When the light converging point 309 is located at a position shown in FIG. 21(a), the reflected light from each reflecting surface of an eye ball is unable to pass the spatial filter 307 and hardly made incident to the light receiving device 308. When the objective lens 305 is brought nearer toward the testing eye 103 in the direction of the optical axis $O_3$ as shown in FIGS. 21(b) and 21(c), the reflected light starts passing through the spatial filter 307 from the outer surface of the cornea 120 from the time the light converging point 309 is brought into generally coincident with the outer surface of the cornea 120. Accordingly, the output of the light receiving device 308 is gradually started to increase and becomes the maximum when the light converging point 309 is brought to be coincident with the outer surface of the cornea 120. That is, a first peak appears for the first time when the light converging point 109 is coincident with the outer surface of the cornea 120. And when the objective lens 305 is brought much nearer to the testing eye 103, a peak appears to the output from the light receiving device 308 based on a reflected light from a rear surface of the cornea, an outer surface of the crystal body 315, etc.

Accordingly, if it is arranged such that the signal processing circuit 313 output a trigger signal and a timing signal based on the first peak, the position detecting circuit 311 detects the position of the objective lens 305 when the light converging point 309 is located at the outer surface of the cornea 120, and the calculating circuit 314 calculates a distance from the reference position to the corneal vertex 120P based on the position of the objective lens 305. At the same time, the measurement of the distance to the eye fundus is started based on the trigger signal.

Figure 22:
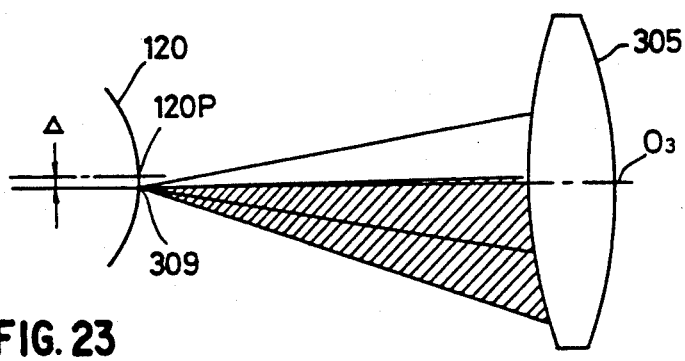

According to this confocal optical system, if the number of apertures (N.A.) of the objective lens 305 is designed to be sufficiently large, even when the light converging point 309 is slightly displaced from the corneal vertex 120P in the direction perpendicular to the optical axis $O_3$ as shown in FIG. 22, the light receiving device 308 can receive almost all amount of the reflected light from the outer surface of the cornea 120 as long as the outer surface of the cornea 120 and the light converging point 309 are coincident with each other. As a result, an alignment error of the measuring instrument with respect to the cornea 120 can be allowed.

Figure 23:
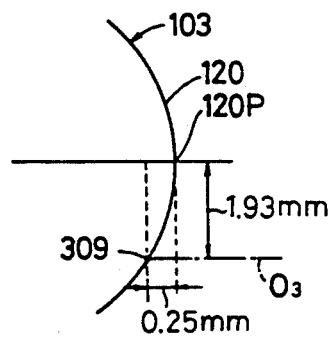

For example, if the radius R of curvature of the cornea 120 is set to 7.7 mm and the number of apertures, in which no reflected light is made incident to the objective lens 305 at all, is set to 0.25, the displacement amount Δ of the light converging point 309 becomes 1.93 mm with respect to the corneal vertex 120P in the direction perpendicular to the optical axis $O_3$. However, if the light converging point 309 is displaced by 1.93 mm with respect to the corneal vertex 120P in the direction perpendicular to the optical axis $O_3$, the position of the light converging point 309 is displaced in the direction of the optical axis $O_3$ by 0.25 mm with respect to the actual corneal vertex 120P as shown in FIG. 23. Therefore, the displacement amount $\Delta$ cannot be designed to so large as approximately 1.93 mm. However, if the displacement amount $\Delta$ is designed to be approximately 0.5 mm, the actual positional displacement of the light converging point 309 with respect to the corneal vertex 120P in the direction of the optical axis is approximately 0.016 mm, and the positional displacement of the light converging point 309 in the direction of the optical axis can be disregarded. It is noted here that in FIG. 22, the portion indicated with a phantom lines indicates a reflected light from the cornea.

Figure 24:
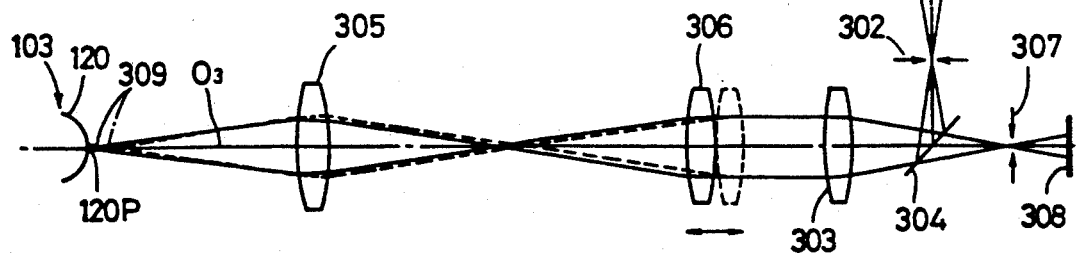

FIG. 24 shows a modified embodiment of the cornea distance detecting system, in which the collimate lens 303 is disposed between the objective lens 305 and the beam splitter 304, a lens 306 is disposed between the collimate lens 303 and the objective lens 305, the lens 306 is movable forward and backward in the direction of the optical axis and the light converging point 309 is movable forward and backward in the direction of the optical axis. In this case, by detecting the position of the lens 306, a distance from the corneal vertex 120P to the reference position of the measuring instrument is measured.

In the above-mentioned embodiment, description has been made on a case wherein the model eye unit 141 is formed on both the cornea and the eye fundus and the length of the eye axis is measured. However, the present invention may likewise be applied to a case wherein this is set to each surface of the crystal body or to each inner surface of the cornea, etc. thereby carrying out a measurement of intraocular length between each planes.

In the intraocular length measuring instrument according to the present invention, the position of the cornea is measured using an optical system in which a principle of geometrical optics is employed, and the position of the eye fundus is measured using an optical system in which a principle of physical optics is employed. Accordingly, an alignment error can be allowed and the measurement becomes easier compared with the eye axis length measuring instrument in which the length of eye axis is measured by interfering the reflected light from the cornea with the reflected light from the eye fundus.

What is claimed is:

1. An intraocular length measuring instrument including:
   a light source having a short coherent length;
   a beam splitter for forming a measuring optical path via the interior of an eye to be tested and a reference optical path within said instrument, and guiding a beam of light from said light source to both said measuring optical path and said reference optical path;
   a first light receiving portion for interfering light reflected by an intraocular object to be measured after passing along said measuring optical path with light coming through said reference optical path and receiving a resultant interference light;
   an intraocular object position measuring portion for finding an optical path difference from an optical path length of said reference optical path and a peak position of a signal coming from said first light receiving portion;
   a light irradiating optical system for irradiating a light beam to the cornea of said eye to be tested;
   a light receiving optical system for introducing a reflected light from said cornea to a second light receiving portion; and
   a corneal position measuring portion for finding a position of said cornea from an output of said second light receiving portion.

2. An intraocular length measuring instrument according to claim 1, wherein said light receiving optical system comprises a first light receiving optical system comprising an objective lens for guiding a reflected light from said cornea to a second light receiving portion through a first diaphragm which is disposed in such a manner as to be conjugate with a front part of said objective lens; and a second light receiving system for guiding a reflected light from said cornea to said second light receiving portion through a second diaphragm which is disposed in such a manner as to be conjugate with a rear part of said second diaphragm;
   said cornea position measuring portion finding a position of said cornea from a position at said second light receiving portion of a reflected light beam from said eye to be tested, which has passed through said first diaphragm and second diaphragm.

3. An introcular length measuring instrument according to claim 1, wherein said light irradiating optical system is adapted to irradiate a parallel beam of light to said cornea;
   said light receiving optical system comprising an objective lens portion for receiving a reflected light from said cornea, and a diaphragm disposed to a rear focusing position thereof;
   a second light receiving portion receiving light through said objective lens portion and said diaphragm;
   said cornea position measuring portion finding a position of said cornea from the light receiving position at said second light receiving portion.

4. An intraocular length measuring instrument according to claim 1, wherein said light irradiating optical system comprises a point light source for irradiating said cornea, and an objective lens portion for forming an image of said point light source in the vicinity of said cornea in such a manner as to be changeable in position;
   said light receiving optical system comprising a beam splitter for splitting a reflected light from said cornea from said light irradiating optical system after the same passes through said objective lens, and a second diaphragm disposed in a conjugate position with an image of said point light source with respect to said objective lens portion;
   a second light receiving portion receiving light among a reflected light from said cornea through said second diaphragm;
   said cornea position measuring portion finding a position of said cornea from intensity of a signal of said second light receiving portion corresponding to change in position of an image of said point light source formed by said objective lens portion;
   said intraocular length being found from said eye fundus position measuring portion and said cornea position measuring portion.

* * * * *